United States Patent
Watkins et al.

(10) Patent No.: US 11,591,542 B2
(45) Date of Patent: Feb. 28, 2023

(54) FRAGRANCE COMPOSITION AND SANITARY OR INCONTINENCE ARTICLE

(71) Applicant: GIVAUDAN SA, Vernier (CH)

(72) Inventors: Stephen David Watkins, Whyteleafe (GB); Sarah Birch, Tankerton (GB)

(73) Assignee: GIVAUDAN SA, Vernier (CH)

( * ) Notice: Subject to any disclaimer, the term of this patent is extended or adjusted under 35 U.S.C. 154(b) by 675 days.

(21) Appl. No.: 16/486,663

(22) PCT Filed: Mar. 7, 2018

(86) PCT No.: PCT/EP2018/055683
§ 371 (c)(1),
(2) Date: Aug. 16, 2019

(87) PCT Pub. No.: WO2018/162603
PCT Pub. Date: Sep. 13, 2018

(65) Prior Publication Data
US 2021/0139810 A1 May 13, 2021

(30) Foreign Application Priority Data

Mar. 8, 2017 (GB) ..................... 1703706

(51) Int. Cl.
*C11B 9/00* (2006.01)
*A61L 15/46* (2006.01)

(52) U.S. Cl.
CPC ............ *C11B 9/0049* (2013.01); *A61L 15/46* (2013.01); *C11B 9/0034* (2013.01)

(58) Field of Classification Search
CPC .................................................. C11B 9/0049
See application file for complete search history.

(56) References Cited

U.S. PATENT DOCUMENTS

| 4,343,783 A | 8/1982 | Hooper et al. |
| 5,733,272 A | 3/1998 | Brunner et al. |
| 2013/0230479 A1 | 9/2013 | Perring et al. |
| 2016/0304806 A1* | 10/2016 | Behan ................... C11B 9/0003 |

FOREIGN PATENT DOCUMENTS

| EP | 1195099 A2 | 4/2002 |
| EP | 3103523 A1 | 12/2016 |
| GB | 2012165 A | 7/1979 |
| JP | 2014508121 A | 4/2014 |
| JP | 2015537099 A | 12/2015 |
| WO | 9851248 A1 | 11/1998 |
| WO | 0226272 A1 | 4/2002 |
| WO | 2012085287 A1 | 6/2012 |
| WO | 2014093807 A1 | 6/2014 |
| WO | 2016049389 A1 | 3/2016 |

OTHER PUBLICATIONS

International Search Report and Written Opinion of the International Searching Authority for corresponding application PCT/EP2018/055683 dated Apr. 18, 2018.
GB Search Report for corresponding application GB 1703706.0 dated Sep. 8, 2017.

* cited by examiner

*Primary Examiner* — Arrie L Reuther
(74) *Attorney, Agent, or Firm* — Norris McLaughlin PA

(57) ABSTRACT

A fragrance composition for use with a sanitary or incontinence article in the treatment of malodour caused by or associated with human body fluids, wherein said composition has an odour that is reminiscent of the odour of the article, as such, or the odour of the packaging material for said article, as such.

13 Claims, 5 Drawing Sheets

FRAGRANCE COMPOSITION AND SANITARY OR INCONTINENCE ARTICLE

This is an application filed under 35 USC 371 based on PCT/EP2018/055683, filed 07.Mar.2018, which in turn is based on GB 1703706.0 filed 08.Mar.2017. The present application claims the full priority benefit of these prior applications and herein incorporates by reference the full disclosures of these prior applications.

The present invention is concerned with fragrance compositions that are malodour counteracting. The invention also relates to the use of said fragrance compositions for the amelioration or elimination of malodours, and in particular those malodours caused by or associated with human body fluids, such as blood, menses and urine. The invention also relates to sanitary or incontinence articles comprising said fragrance compositions.

Fragrances play an important role in the management of both human and environmental malodour by masking or eliminating the malodour, and they are almost universally appreciated as such, for the relief they can provide from the distress and discomfort that bad smells can elicit in people.

With regard to sanitary or incontinence articles used to absorb body fluids, such as blood, menses or urine, however, the often strong and characteristic odour of fragrance compositions employed to counteract malodour can create a negative association in the minds of users of these articles, and others around them. More specifically, the strong and characteristic odour of the fragrances employed in these articles can act as an olfactive signal that the user has an incontinence or sanitary problem.

This presents a problem for manufacturers of such articles, as well as the consumers who depend upon them. Malodour counteraction is concerned not merely with the aesthetic consideration of hiding unpleasant smells. The successful control of this type of malodour can foster positive social impact within communities. Taking the population living within incontinence for example, for these people, well-being starts with cleanliness, and if they are deterred from using incontinence articles because they are heavily perfumed, they can become alienated from their communities, with all the negative social impact this entails.

For the female population too, and particularly adolescent females, the use of sanitary articles enables them to pursue more active lives during periods of menstruation. Access to discrete sanitary articles reinforces confidence in their use and can increase the sense of empowerment for many females, particularly adolescent females.

For the manufacturers of sanitary and incontinence articles, it is imperative that when consumers open a package of such articles, or interact with the articles, they are not overwhelmed with a strong or characteristically fragrant odour. Consumers will not appreciate the experience and may be disinclined to make repeat purchases as a result.

Manufacturers of these articles also realise the importance of contributing to a sustainable society that enriches the lives of its people, and particularly vulnerable groups, and understand the need to develop innovative products that foster well-being in the aged and incontinent population, as well as those that foster empowerment in females, and particularly adolescent females. Their success depends upon building close connections with consumers by developing products that promote well-being, by focusing particularly on issues related to aging populations, health, cleanliness and hygiene. Functional and acceptable malodour-counteracting perfumery is a key driver to this drive for success.

In the field of sanitary and incontinence articles, the prior art teaches the desirability of using deodorizing fragrances that have relatively low odour intensity, or alternatively, proposes the application of only low doses of fragrance to sanitary and incontinence articles. Examples of fragrance compositions useful in incontinence and sanitary products are described in WO 2004/098666 and WO 2004/098667.

However, a problem attendant with the use of low odour intensity fragrances or low levels of fragrance is the reduced ability to mask malodour. Furthermore, the fragrance ingredients proposed as being useful possess characterful odours that are recognizable to consumers as being perfumistic when smelled in context with sanitary and incontinence articles. It will be obvious to the consumer that the articles are fragranced, in other words.

There remains a need to provide discrete-smelling yet effective fragrance compositions, which are malodour counteracting, and which are particularly suitable for use in articles for the reduction or elimination of malodour associated with human body fluids.

Figure 1:
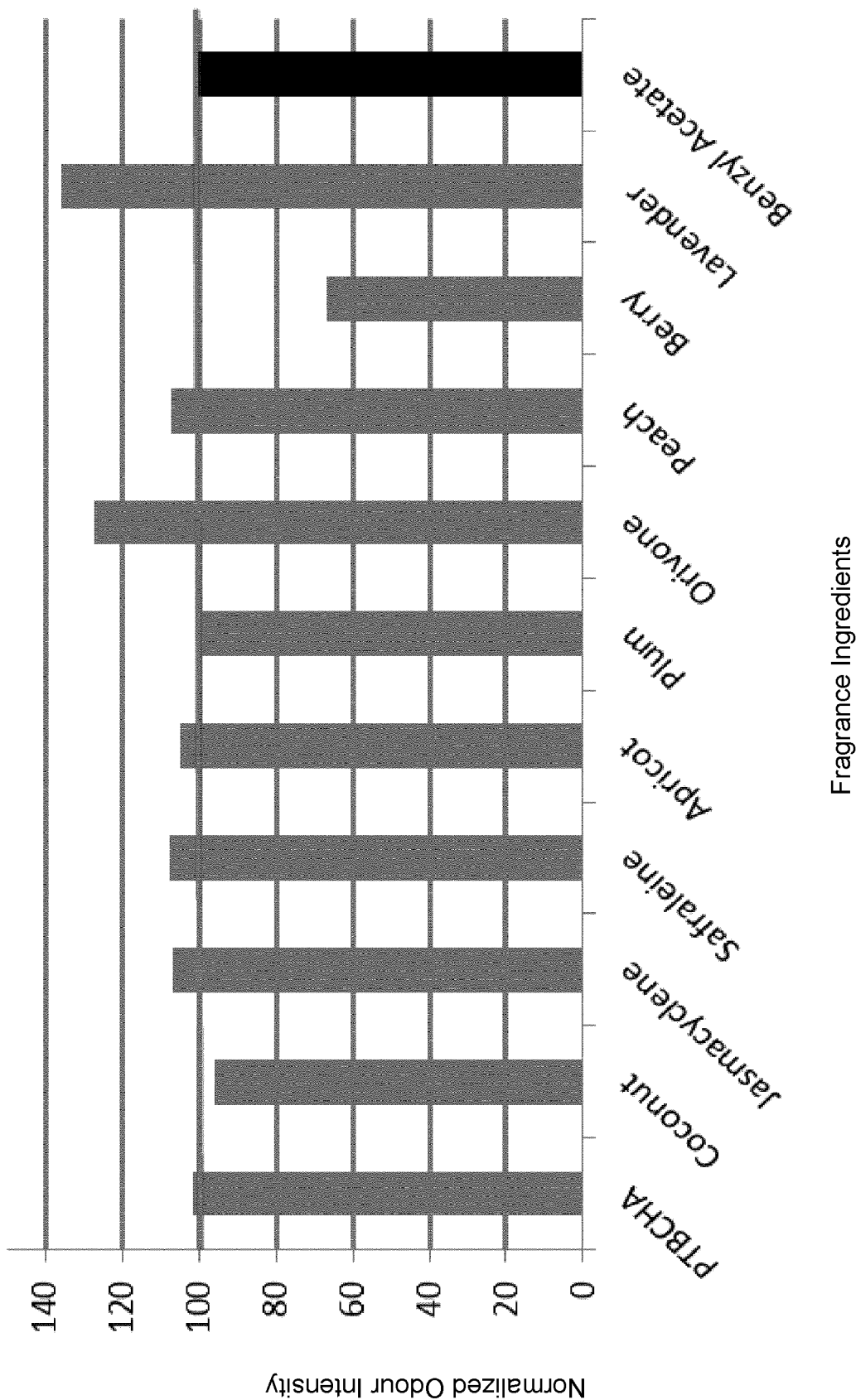
FIG. 1 depicts normalized odour intensity data for the fragrance compositions and fragrance ingredients, relevant to Example 1.

Accordingly, the disclosure provides in a first aspect a fragrance composition for use with a sanitary or incontinence article to counteract malodour caused by or associated with human body fluids, wherein said composition has an odour that is reminiscent of the odour of the article, as such, or the odour of the packaging material for said article, as such.

In another aspect, the disclosure provides a sanitary or incontinence article comprising the fragrance composition defined herein, in particular an adult incontinence article.

In yet another aspect, the disclosure provides a method of preventing or ameliorating malodour caused by or associated with human body fluids such as blood, menses or urine, said method comprising the step of providing a sanitary or incontinence article containing a fragrance composition defined herein, together with instructions to place the article on, in or about the human body proximate to a body waste discharge area.

In still another aspect, the disclosure provides a method of promoting cleanliness, hygiene and/or well-being in incontinent populations or female populations, said method comprising the step of providing a sanitary or incontinence article containing a fragrance composition defined herein, together with instructions to place the article on, in or about the human body proximate to a body waste discharge area.

In yet another aspect, the disclosure provides the use of a fragrance composition as defined herein in combination with a sanitary or incontinence article to prevent or ameliorate malodour caused by or associated with human body fluids such as blood, menses or urine.

These and other aspects and embodiments of the invention will be described below in the detailed description and examples.

Contrasting prior art malodour-counteracting fragrance compositions used in sanitary and incontinence products, a fragrance composition of the present invention has a characteristically high odour intensity; however, because its odour is reminiscent of the neutral or inoffensive odour of the article or its packaging as such, the consumer does not associate its odour with the presence of a fragrance composition. In essence, the consumer perceives an unfragranced article. This enables the formulator to use sufficiently high doses of the fragrance composition in order to exert a strong malodour-counteracting effect. In this way, efficacious and long-lasting malodour control can be achieved in a discrete way.

Surprisingly, the applicant has discovered fragrance compositions consisting of single fragrance ingredients or blends of fragrance ingredients that when applied to sanitary or incontinence articles and/or their packaging, are indistinguishable, or substantially so, from the odour of the articles as such, or packaging containing them. More particularly, the applicant discovered that panellists were unsure, or unable to associate the odour of the fragrance compositions as belonging to a fragrance as such. In fact, panellists were inclined in the main to ascribe the odour they perceived to the odour of the article as such, or its packaging, and not a fragrance, as such.

This finding has important consequences for the design of fragrance compositions having a malodour-counteracting effect that can be usefully incorporated into articles that are adapted to address incontinence and hygiene, such as urinary incontinence—in particular adult incontinence—and feminine hygiene.

As used herein, the term sanitary or incontinence article(s) is used to describe articles, usually absorbent articles, irrespective of form, that are adapted to be placed in, on, or about the human body, usually adjacent to an area or site of body discharge, in order to collect discharge, and by means of the fragrance composition having a malodour-counteracting effect contained therein, to prevent or ameliorate malodour caused by or associated with human body fluids, and in particular blood, menses or urine.

Fragrance compositions of the present invention must be sufficiently intense in order to provide a malodour-counteracting effect, but they should not, in the context in which they are employed, be perceived as being perfumistic; that is, they should be perceived by consumers as resembling the odour of the article into which they are incorporated, or its packaging, rather than the odour of a fragrance as such.

In order to achieve this, fragrance compositions of the present invention must comprise sufficient quantities of fragrance ingredients of requisite odour intensity, which also have an odour character that is neutral—or non-perfumistic—in the context in which it is smelled.

Odour intensity can be assessed in an objective and straightforward manner according to generally known test protocols. Odour intensity of fragrance ingredients and fragrance compositions according to the present invention is measured in accordance with the following protocol:

Samples of individual test fragrance ingredients or test fragrance compositions are used either neat or as a dilution. A sample of 5% benzyl acetate in dipropylene glycol is used as an intensity reference.

1.5 g (+/−0.1 g) of each sample is placed into a small (approx. 7 ml) glass wide-neck jar with screw lid. Panellists assess and score the intensity from the jars using a 0-10 scale (0=no perceived intensity, 10=extremely high intensity) and each panellist assesses all samples, including the intensity reference sample (5% benzyl acetate in dipropylene glycol). The resulting individual panellist intensity scores for each test sample are normalised relative to the 5% benzyl acetate using the following equation:

"Normalised intensity=Intensity of Test Sample/Intensity of Benzyl Acetate×100"

The normalised values for each test sample were combined across all panellists to give a consensus value for the whole panel (arithmetic mean).

"Odour Intensity Index=Sum of Normalised Intensity/Number of Panellists"

In this way, the intensity of the test samples can be shown relative to the intensity of 5% benzyl acetate, which is assigned a value of 100.

For the purpose of the present invention, only those test fragrance ingredients or fragrance compositions having a score of 100 or more relative to the 5% benzyl acetate dilution, in accordance with the test protocol referred to hereinabove, are considered to be of sufficiently high odour intensity for fragrance compositions of the present invention.

Fragrance ingredients having an odour intensity of more than 100 ("high odour intensity ingredients") may be selected from the group consisting of: -2-methyl-pent-2-enoic acid; 1,1-diethoxyethane (for example ACETAL); (2-(1-ethoxyethoxy)ethyl)benzene (for example ACETAL E); 1-(4-methoxyphenyl)ethanone (for example ACETANISOLE); 3-hydroxybutan-2-one (for example ACETOIN); 1-phenylethanone (for example ACETOPHENONE EXTRA); 1-(2-pyrazinyl)ethanone (for example ACETYL PYRAZINE); 1-(thiazol-2-yl)ethanone (for example ACETYL THIAZOLE); 2-(tert-butyl)cyclohexyl acetate (for example AGRUMEX); hexan-1-ol (for example ALCOHOL C 6 HEXYLIC); octan-1-ol (for example ALCOHOL C 8 OCTYLIC); nonan-1-ol (for example ALCOHOL C 9 NONYLIC); decanal (for example ALDEHYDE C 10 DECYLIC); undecanal (for example ALDEHYDE C 11); undec-10-enal (for example ALDEHYDE C 11 UNDECYLENIC); undecanal (for example ALDEHYDE C 110 UNDECYLIC); dodecanal (for example ALDEHYDE C 12); 2-methylundecanal (for example ALDEHYDE C 12 MNA); hexanal (for example ALDEHYDE C 6 HEXYLIC) heptanal (for example ALDEHYDE C 7 HEPTYLIC) octanal (for example ALDEHYDE C 8); 3,5,5-trimethylhexanal (for example ALDEHYDE C 9 ISONONYLIC); nonanal (for example ALDEHYDE C 9 NONYLIC); (E)-undec-9-enal (for example ALDEHYDE ISO C 11); allyl 2-(isopentyloxy)acetate (for example ALLYL AMYL GLYCOLATE); allyl hexanoate (for example ALLYL CAPROATE); allyl 3-cyclohexylpropionate (for example ALLYL CYCLOHEXYL PROPIONATE); allyl heptanoate (for example ALLYL OENANTHATE); decahydro-2,2,6,6,7,8,8-heptamethyl indenofuran (for example AMBER XTREME); (4aR,5R,7aS,9R)-Octahydro-2,2,5,8,8,9a-hexamethyl-4H-4a,9-methanoazuleno[5,6-d]-1,3-dioxole (for example AMBROCENIDE); (4aR,5R,7aS,9R)-Octahydro-2,2,5,8,8,9a-hexamethyl-4H-4a,9-methanoazuleno[5,6-d]-1,3-dioxole (for example AMBROCENIDE CRYSTALS); (3aR,5aS,9aS,9bR)-3a,6,6,9a-tetramethyl-2,4,5,5a,7,8,9,9b-octahydro-1H-benzo[e][1]benzofuran (for example AMBROFIX); (3aR,5aS,9aS,9bR)-3a,6,6,9a-tetramethyl-2,4,5,5a,7,8,9,9b-octahydro-1H-benzo[e][1]benzofuran (for example AMBROXAN); pentyl butanoate (for example AMYL BUTYRATE); 1-octene-3-ol (for example AMYL VINYL CARBINOL); (E)-1-methoxy-4-(prop-1-en-1-yl) benzene (for example ANETHOLE SYNTHETIC); (4-methoxyphenyl)methanol (for example ANISYL ALCO- HOL); 1-phenylethanethiol (for example ANJERUK); 4-methoxybenzaldehyde (for example AUBEPINE PARA CRESOL); (E)-methyl 2-((7-hydroxy-3,7-dimethyloctyl-idene)amino)benzoate (for example AURANTIOL); 3,5-diethyl-2,5-dimethylcyclohex-2-enone (for example AZAR-BRE); 7-isopentyl-2H-benzo[b][1,4]dioxepin-3(4H)-one (for example AZURONE); benzaldehyde; benzyl acetate; 4-phenylbutan-2-one (for example BENZYL ACETONE); benzyl formate; benzyl isobutanoate (for example BENZYL ISOBUTYRATE); (methoxymethyl)benzene (for example BENZYL METHYL ETHER); octahydro-2H-chromen-2-one (for example BICYCLO NONALACTONE); 8-(sec-butyl)-5,6,7,8-tetrahydroquinoline (for example BIG-ARYL); (1S,2S,4S)-1,7,7-trimethylbicyclo[2.2.1]heptan-2-ol (for example BORNEOL CRYSTALS); (2S,4S)-1,7,7-trimethylbicyclo[2.2.1]heptan-2-yl acetate (for example BORNYL ACETATE LIQUID); 3-(4-(tert-butyl)phenyl) propanal (for example BOURGEONAL); butyl acetate; butyl butanoate (for example BUTYL BUTYRATE); 4-(tert-butyl)cyclohexyl acetate (for example BUTYL CYCLO-HEXYL ACETATE PARA); 6-butan-2-ylquinoline (for example BUTYL QUINOLINE); butanoic acid (for example BUTYRIC ACID); 1,2,4-trimethoxy-5-propylbenzene (for example CALMODE); 6-methoxy-2,6-dimethyloctanal (for example CALYPSONE); 2-isobutyl-5-methyl-1,3-dioxane (for example CAMONAL); (1S,4S)-1,7,7-trimethylbicyclo[2.2.1]heptan-2-one (for example CAMPHOR); 3-hydroxy-4,5-dimethylfuran-2(5H)-one (for example CARAMEL LACTONE); 5-isopropyl-2-methylphenol (for example CARVACROL); (5R)-2-methyl-5-prop-1-en-2-ylcyclohex-2-en-1-one (for example CARVONE LAEVO); 5-tert-butyl-2-methyl-5-propyl-2H-furan (for example CASSYRANE); (1S,8aR)-1,4,4,6-tetramethyl-2,3,3a,4,5,8-hexahydro-1H-5, 8a-methanoazulene (for example CEDRENE); 3-methyl-5-propylcyclohex-2-enone (for example CELERY KETONE); (E)-3-phenylprop-2-en-1-ol (for example CINNAMIC ALCOHOL); (2E)-3-phenylprop-2-enal (for example CIN-NAMIC ALDEHYDE); (E)-3,7-dimethylocta-2,6-dienal (for example CITRAL); 3,7-dimethyloct-6-enal (for example CITRONELLAL); 3,7-dimethyloct-6-en-1-ol (for example CITRONELLOL); 3,7-dimethyloct-6-enenitrile (for example CITRONELLYL NITRILE); 2-((3,7-dimethyloct-6-en-1-yl)oxy)acetaldehyde (for example CITRO-NELLYL OXYACETALDEHYDE); 2,4,4,7-tetramethyloct-6-en-3-one (for example CLARITONE); dodecanenitrile (for example CLONAL); 2-(2-mercaptopropan-2-yl)-5-methylcyclohexanone (for example CORPS CASSIS); (4S)-4,7,7-trimethyl-6-thiabicyclo[3.2.1]octane (for example CORPS PAMPLEMOUSSE); (Z)-3-methylcyclotetradec-5-enone (for example COSMONE); 2H-chromen-2-one (for example COUMARIN PURE CRYSTALS); 2-methoxy-4-methylphenol (for example CREOSOL); p-cresol (for example CRESOL PARA); (4-methylphenyl) acetate (for example CRESYL ACETATE PARA); (4-methylphenyl) octanoate (for example CRESYL CAPRYLATE PARA); (4-methylphenyl) 2-methylpropanoate (for example CRE-SYL ISOBUTYRATE PARA); 1-methoxy-4-methylbenzene (for example CRESYL METHYL ETHER PARA); ethyl 2,6,6-trimethylcyclohexa-1,3-diene-1-carboxylate (for example CRISTALON); 4-isopropylbenzonitrile (for example CUMIN NITRILE); 4-isopropylbenzaldehyde (for example CUMINIC ALDEHYDE); 2,4-dimethylcyclohex-3-ene-1-carbaldehyde (for example CYCLAL C); 3-(4-isopropylphenyl)-2-methylpropanal (for example CYCLA-MEN ALDEHYDE); allyl 2-(cyclohexyloxy)acetate (for example CYCLOGALBANATE); 4-(4-hydroxy-4-methylpentyl)cyclohex-3-enecarbaldehyde (for example CYCLO-HEXAL); 2-cyclohexylethyl acetate (for example CYCLO-HEXYL ETHYL ACETATE); 8,8-dimethyl-1,2,3,4,5,6,7,8-octahydronaphthalene-2-carbaldehyde (for example CYCLOMYRAL); 1-methyl-4-propan-2-ylbenzene (for example CYMENE PARA); methyl 1,4-dimethylcyclohexanecarboxylate (for example CYPRISATE); (E)-1-(2,6,6-trimethylcyclohexa-1,3-dien-1-yl)but-2-en-1-one (for example DAMASCENONE); (E)-1-(2,6,6-trimethylcyclohex-2-en-1-yl)but-2-en-1-one (for example DAMASCONE ALPHA); (E)-1-(2,6,6-trimethyl-1-cyclohexenyl)but-2-en-1-one (for example DAMASCONE BETA); 1-(2,6,6-trimethyl-1-cyclohex-3-enyl)but-2-en-1-one (for example DAMASCONE DELTA); 6-pentyltetrahydro-2H-pyran-2-one (for example DECALACTONE DELTA); 5-hexyloxolan-2-one (for example DECALACTONE GAMMA); decanenitrile (for example DECANONITRILE); (E)-dec-2-enal (for example DECENAL-2-TRANS); (E)-dec-4-enal (for example DECENAL-4-TRANS); (1S,6S)-3,7,7-trimethylbicyclo[4.1.0]hept-3-ene (for example DELTA-3 CARENE); diethyl propanedioate (for example DIETHYL MALONATE); 1-methoxy-4-propylbenzene (for example DIHYDRO ANETHOLE); 2-methoxy-4-propylphenol (for example DIHYDRO EUGENOL); 4-(2,6,6-trimethylcyclohex-1-en-1-yl)butan-2-one (for example DIHYDRO ION-ONE BETA); 3-methyl-2-pentylcyclopent-2-enone (for example DIHYDRO JASMONE); 3,7-dimethyloct-6-en-3-ol (for example DIHYDRO LINALOOL); 2,6-dimethyloct-7-en-2-ol (for example DIHYDRO MYRCENOL); 2-(4-methylcyclohexyl)propan-2-ol (for example DIHYDRO TERPINEOL); methyl 2-(methylamino)benzoate (for example DIMETHYL ANTHRANILATE); 2-methyl-1-phenylpropan-2-yl acetate (for example DIMETHYL BENZYL CARBINYL ACETATE); 1,4-dimethoxybenzene (for example DIMETHYL HYDROQUINONE); 4,7-dimethyloct-6-en-3-one (for example DIMETHYL OCTENONE); dimethyl sulfide 1%; 2,6-dimethylheptan-2-ol (for example DIMETOL); 2,6-dimethyloct-7-en-2-ol (for example DIMYRCETOL); 2-(2-(3,3,5-trimethylcyclohexyl)acetyl)cyclopentanone (for example DIONE); 1-methyl-4-(prop-1-en-2-yl)cyclohex-1-ene (for example DIPENTENE); oxydibenzene (for example DIPHENYL OXIDE); 5-octyloxolan-2-one (for example DODECALACTONE GAMMA); (E)-dodec-2-enal (for example DODECENAL); (E)-4-((3aS,7aS)-hexahydro-1H-4,7-methanoinden-5(6H)-ylidene)butanal (for example DUPICAL); (E)-3-methyl-5-(2,2,3-trimethylcyclopent-3-en-1-yl)pent-4-en-2-ol (for example EBANOL); 3-(1-ethoxyethoxy)-3,7-dimethylocta-1,6-diene (for example ELINTAAL); 1-allyl-4-methoxybenzene (for example ESTRAGOLE); ethyl acetate (for example ETHYL ACETATE); ethyl 3-oxobutanoate (for example ETHYL ACETOACETATE); octan-3-one (for example ETHYL AMYL KETONE); ethyl benzoate; ethyl butanoate (for example ETHYL BUTYRATE); ethyl 3-phenylprop-2-enoate (for example ETHYL CINNAMATE); 5-ethyl-2,3-dimethylpyrazine (for example ETHYL DIM-ETHYL PYRAZINE); ethyl hexanoate; 6-methylheptan-3-one (for example ETHYL ISOAMYL KETONE); ethyl 2-methylpropionate (for example ETHYL ISOBU-TYRATE); ethyl 3-methylbutanoate (for example ETHYL ISOVALERATE); (E)-3,7-dimethylnona-1,6-dien-3-ol (for example ETHYL LINALOOL); 2-ethyl-3-hydroxy-4H-pyran-4-one (for example ETHYL MALTOL); ethyl 2-methylbutanoate (for example ETHYL METHYL-2-BU-TYRATE); ethyl octanoate; ethyl heptanoate (for example ETHYL OENANTHATE); ethyl 2-phenylacetate (for example ETHYL PHENYL ACETATE); ethyl 3-phenyloxirane-2-carboxylate (for example ETHYL PHENYL GLYCI- DATE); ethyl propionate; ethyl 2,6,6-trimethylcyclohexa-1,3-diene-1-carboxylate (for example ETHYL SAFRANATE); ethyl 2-hydroxybenzoate (for example ETHYL SALICYLATE); 3-ethoxy-4-hydroxybenzaldehyde (for example ETHYL VANILLIN); 2-ethyl-3-methylpyrazine; (1s,4s)-1,3,3-trimethyl-2-oxabicyclo[2.2.2]octane (for example EUCALYPTOL); 4-allyl-2-methoxyphenol (for example EUGENOL); 1,3,3-trimethylbicyclo[2.2.1]heptan-2-one (for example FENCHONE ALPHA); (1S,2R,4R)-1,3,3-trimethylbicyclo[2.2.1]heptan-2-ol (for example FENCHYL ALCOHOL); (E)-5-methylhept-2-en-4-one (for example FILBERTONE); 3a,6,6,9a-tetramethyldodecahydronaphtho[2,1-b]furan (for example FIXAMBRENE); 3-(4-ethylphenyl)-2,2-dimethylpropanal (for example FLORALOZONE); 3-(3-isopropylphenyl)butanal (for example FLORHYDRAL); (E)-undec-9-enenitrile (for example FLORIDILE); (3aR,6S,7aS)-3a,4,5,6,7,7a-hexahydro-1H-4,7-methanoinden-6-yl propionate (for example FLOROCYCLENE); 2,4,6-trimethyl-4-phenyl-1,3-dioxane (for example FLOROPAL); tetrahydro-4-methyl-2-(2-methylpropyl)-2H-pyran-4-ol (for example FLOROSA); (Z)-1-(cyclooct-3-en-1-yl)propan-1-ol (for example FLORYMOSS); methyl oct-2-ynoate (for example FOLIONE); 4-isopropylcyclohexanol (for example FOLROSIA); ethyl 2-(2,4-dimethyl-1,3-dioxolan-2-yl)acetate (for example FRAISTONE); ethyl 2-(2-methyl-1,3-dioxolan-2-yl)acetate (for example FRUCTONE); (3aS,4S,7R,7aS)-ethyl octahydro-1H-4,7-methanoindene-3a-carboxylate (for example FRUITATE); 2-methyldecanenitrile (for example FRUTONILE); 1-(5,5-dimethylcyclohex-1-en-1-yl)pent-4-en-1-one (for example GALBANONE); 1-phenylethyl acetate (for example GARDENOL); (3aR,6S,7aS)-3a,4,5,6,7,7a-hexahydro-1H-4,7-methanoinden-6-yl 2-methyl propanoate (for example GARDOCYCLENE); 1-(1,2,8,8-tetramethyl-1,2,3,4,5,6,7,8-octahydronaphthalen-2-yl)ethanone (for example GEORGYWOOD); (E)-3,7-dimethylocta-2,6-dien-1-ol (for example GERANIOL, GERANIOL PALMAROSA); 2-(2-hydroxypropan-2-yl)-5-methylcyclohexanol (for example GERANODYLE); (E)-6,10-dimethylundeca-5,9-dien-2-one (for example GERANYL ACETONE); (E)-3,7-dimethylocta-2,6-dien-1-yl formate (for example GERANYL FORMATE); 3a-ethyl-6,6,9a-trimethyldodecahydronaphtho[1,2-c]furan (for example GRISALVA); 2-methoxyphenol (for example GUAIACOL); 2-butyl-4,6-dimethyl-3,6-dihydro-2H-pyran (for example GYRANE); methyl 3-oxo-2-pentyl-cyclopentaneacetate (for example HEDIONE, HEDIONE HC, CEPIONATE, and METHYL DIHYDROJASMONATE); 5-propyloxolan-2-one (for example HEPTALACTONE GAMMA); heptan-2-one (for example HEPTONE); (2S)-ethyl 3-isopropylbicyclo[2.2.1]hept-5-ene-2-carboxylate (for example HERBANATE); (3R,5R)-3-ethoxy-1,1,5-trimethylcyclohexane (for example HERBAVERT); (E)-hex-2-enal (for example HEXENAL-2-TRANS); (E)-hex-2-en-1-ol (for example HEXENOL TRANS-2); (Z)-hex-3-en-1-ol (for example HEXENOL-3-CIS); (Z)-hex-3-en-1-yl acetate (for example HEXENYL-3-CIS ACETATE); (Z)-hex-3-en-1-yl butanoate (for example HEXENYL-3-CIS BUTYRATE); (Z)-hex-3-en-1-yl formate (for example HEXENYL-3-CIS FORMATE); (Z)-hex-3-en-1-yl (Z)-hex-3-enoate (for example HEXENYL-3-CIS HEXENOATE); (Z)-hex-3-en-1-yl isobutanoate (for example HEXENYL-3-CIS ISOBUTYRATE); (Z)-hex-3-en-1-yl 2-methyl butanoate (for example HEXENYL-3-CIS METHYL-2-BUTYRATE); (Z)-hex-3-en-1-yl propionate (for example HEXENYL-3-CIS PROPIONATE); (Z)-hex-3-enyl] (E)-2-methylbut-2-enoate (for example HEXENYL-3-CIS TIGLATE); hexyl acetate (for example HEXYL ACETATE); hexyl propionate; 2-ethyl-4-hydroxy-5-methylfuran-3(2H)-one (for example HOMOFURONOL); 2-phenylpropanal (for example HYDRATROPIC ALDEHYDE); (1,1-dimethoxypropan-2-yl)benzene (for example HYDRATROPIC ALDEHYDE DIMETHYL ACETAL); 1H-indole (for example INDOLE PURE); 8,8-di(1H-indol-3-yl)-2,6-dimethyloctan-2-ol (for example INDOLENE); (E)-4-(2,6,6-trimethylcyclohex-1-en-1-yl)but-3-en-2-one (for example IONONE BETA); (E)-3-methyl-4-(2,6,6-trimethylcyclohex-2-en-1-yl)but-3-en-2-one (for example IRISANTHEME); (E)-4-(2,6,6-trimethylcyclohex-2-en-1-yl)but-3-en-2-one (for example IRISONE ALPHA and IRISONE PURE); (E)-4-(2,5,6,6-tetramethylcyclohex-2-en-1-yl)but-3-en-2-one (for example IRONE ALPHA); 1-(2,3,8,8-tetramethyl-1,2,3,4,5,6,7,8-octahydronaphthalen-2-yl)ethanone (for example ISO E SUPER); 3-methylbutyl acetate (for example ISOAMYL ACETATE); 3-methylbutyl butanoate (for example ISOAMYL BUTYRATE); 3-methylbutyl propionate (for example ISOAMYL PROPIONATE); 4-formyl-2-methoxyphenyl isobutanoate (for example ISOBUTAVAN); 2-methylpropyl benzoate (for example ISOBUTYL BENZOATE); 2-methylpropyl 2-methylpropanoate (for example ISOBUTYL ISOBUTYRATE); 2-methylpropyl 3-methoxypyrazine (for example ISOBUTYL METHOXY PYRAZINE); 2-methylpropyl 2-phenylacetate (for example ISOBUTYL PHENYL ACETATE); 6-butan-2-yl-quinoline (for example ISOBUTYL QUINOLINE-2); 2,4,6-trimethylcyclohex-3-enecarbaldehyde (for example ISOCYCLOCITRAL); (E)-2-methoxy-4-(prop-1-en-1-yl)phenol (for example ISOEUGENOL); 2-methoxy-3-(4-methylpentyl)pyrazine (for example ISOHEXYLMETHOXY PYRAZINE); 2-hexylcyclopent-2-enone (for example ISOJASMONE); 2-isopropyl-5-methylcyclohexanone (for example ISOMENTHONE); 3-methylbutyl 3-methylbutanoate (for example ISOPENTYL ISOVALERATE); 4-methylpent-4-en-2-yl 2-methylpropanoate (for example ISOPENTYRATE); isopropyl 2-methylbutanoate (for example ISOPROPYL METHYL-2-BUTYRATE); 6-isopropylquinoline (for example ISOPROPYL QUINOLINE); 2-isopropyl-4-methylthiazole; 5-methyl-2-(prop-1-en-2-yl)cyclohexanol (for example ISOPULEGOL); (E)-3-methyl-4-(2,6,6-trimethylcyclohex-2-en-1-yl)but-3-en-2-one (for example ISORALDEINE, ISORALDEINE CETONE ALPHA and ALPHA ISOMETHYL IONONE); (3aR,6S,7aS)-3a,4,5,6,7,7a-hexahydro-1H-4,7-methanoinden-6-yl acetate (for example JASMACYCLENE); 2-hexylcyclopentanone (for example JASMATONE); (Z)-3-methyl-2-(pent-2-en-1-yl) cyclopent-2-enone (for example JASMONE CIS); (1-methyl-2-((1,2,2-trimethylbicyclo[3.1.0]hexan-3-yl)methyl)cyclopropyl)methanol (for example JAVANOL); (4Z)-hept-4-en-2-yl 2-hydroxybenzoate (for example KARMAFLOR); 4-(1-ethoxyethenyl)-3,3,5,5-tetramethylcyclohexan-1-one (for example KEPHALIS); (Z)-3,4,5,6,6-pentamethylhept-3-en-2-one (for example KOAVONE); 3,6-dimethyl-3a,4,5,6,7,7a-hexahydro-3H-benzofuran-2-one (for example KOUMALACTONE); 8-isopropyl-1-oxaspiro[4.5]decan-2-one (for example LAITONE); (Z)-1-(1-ethoxyethoxy)hex-3-ene (for example LEAF ACETAL); (2E,6Z)-3,7-dimethylnona-2,6-dienenitrile (for example LEMONILE); 3-(4-(tert-butyl)phenyl)-2-methylpropanal (for example LILIAL); 2,2,6-trimethyl-6-vinyltetrahydro-2H-pyran (for example LIMETOL); 3,7-dimethylocta-1,6-dien-3-ol (for example LINALOOL); bicyclo[2.2.2]oct-5-ene-2-carboxaldehyde (for example MACEAL); 2,4-dimethyl-4,4a,5,9b-tetrahydroindeno[1,2-d][1,3]dioxine (for example MAGNOLAN); (4E)-9-hydroxy-5,9-dimethyl-4-decenal (for example MAHONIAL); 3-hydroxy-2-methyl-4H-pyran-4-one (for example MALTOL); ethyl 2-methylpentanoate (for example MANZANATE); 3-methyl-5-phenylpentanal (for example MEFRANAL); 3-methyl-5-phenylpentan-1-ol (for example MEFROSOL); 2,6-dimethylhept-5-enal (for example MELONAL); tricyclo[5.2.1.02,6]decane-3-carbaldehyde (for example MELOZONE); 2-isopropyl-5-methylcyclohexanone (for example MENTHONE); 2-(4-methylcyclohex-3-en-1-yl)propane-2-thiol (for example MERCAPTO-8 MENTHENE-1 PARA); (2-butan-2-yl-1-methylcyclohexyl) acetate (for example METAMBRATE); 2-methoxy-3-methylpyrazine (for example METHOXY METHYL PYRAZINE); 4-(4-methoxyphenyl)butan-2-one (for example METHOXY PHENYL BUTANONE); 6-methoxy-2,6-dimethylheptanal (for example METHOXYMELONAL); 1-(p-tolyl)ethanone (for example METHYL ACETOPHENONE); heptan-2-one (for example METHYL AMYL KETONE); methyl 2-aminobenzoate (for example METHYL ANTHRANILATE); methyl benzoate (for example METHYL BENZOATE); butyl 2-methylpentanoate (for example METHYL CAMOMILLE); 1-((1S,8aS)-1,4,4,6-tetramethyl-2,3,3a,4,5,8-hexahydro-1H-5,8a-methanoazulen-7-yl)ethanone (for example METHYL CEDRYL KETONE); methyl 3-phenylprop-2-enoate (for example METHYL CINNAMATE); 3,4-dimethylcyclopentane-1,2-dione (for example METHYL CORYLONE); 5-hexyl-5-methyloxolan-2-one (for example METHYL DECALACTONE GAMMA); 2-ethoxy-4-(methoxymethyl)phenol (for example METHYL DIANTILIS); methyl 2-hexyl-3-oxocyclopentane-1-carboxylate (for example METHYL DIHYDRO ISOJASMONATE); (Z)-methyl 2-(3-oxo-2-(pent-2-en-1-yl)cyclopentyl)acetate (for example METHYL EPI JASMONATE); 6-methylhept-5-en-2-one (for example METHYL HEPTENONE PURE); octan-2-one (for example METHYL HEXYL KETONE); 8-methyl-1-oxaspiro[4.5]decan-2-one (for example METHYL LAITONE); methyl 2-methylbutanoate (for example METHYL METHYL-2 BUTYRATE); undecan-2-one (for example METHYL NONYL KETONE); methyl non-2-ynoate (for example METHYL OCTYNE CARBONATE); 6,6-dimethoxy-2,5,5-trimethylhex-2-ene (for example METHYL PAMPLEMOUSSE); methyl 2-phenylacetate (for example METHYL PHENYL ACETATE); methyl 2-hydroxybenzoate (for example METHYL SALICYLATE); 4-methyl-5-pentyldihydrofuran-2(3H)-one (for example METHYL TUBERATE PURE); 2-methyl pyrazine (for example METHYL-2 PYRAZINE); 1a,3,3,4,6,6-hexamethyl-1a,2,3,4,5,6,7,7a-octahydronaphtho[2,3-b]oxirene (for example MOXALONE); 4-(4-methylpent-3-en-1-yl)cyclohex-3-enecarbaldehyde (for example MYRALDENE); 7-methyl-3-methyleneocta-1,6-diene (for example MYRCENE); 2-methylundecanoic acid (for example MYSTIKAL); 2-(2-(4-methylcyclohex-3-en-1-yl)propyl)cyclopentanone (for example NECTARYL); 10-isopropyl-2,7-dimethyl-1-oxaspiro[4.5]deca-3,6-diene (for example NEOCASPIRENE EXTRA); (2Z)-3,7-dimethylocta-2,6-dien-1-ol (for example NEROLEX); 2-ethoxynaphthalene (for example NEROLINE CRYSTALS); 1-(3-methylbenzofuran-2-yl)ethanone (for example NEROLIONE); 1-(3-methylbenzofuran-2-yl)ethanone (for example NEROLIONE); (E)-13-methyloxacyclopentadec-10-en-2-one (for example NIRVANOLIDE); (2E,6Z)-nona-2,6-dienal (for example NONADIENAL); (2Z,6E)-2,6-nonadien-1-ol (for example NONADIENOL-2,6); (2Z,6E)-2,6-nonadien-1-yl acetate (for example NONADIENYL ACETATE); 6,8-dimethylnonan-2-ol (for example NONADYL); (Z)-non-6-enal (for example NONENAL-6-CIS); (Z)-non-6-en-1-ol (for example NONENOL-6-CIS); 3-(4-isobutyl-2-methylphenyl)propanal (for example NYMPHEAL); (E)-3,7-dimethylocta-1,3,6-triene (for example OCIMENE); 6-propyltetrahydro-2H-pyran-2-one (for example OCTALACTONE DELTA); 5-butyloxolan-2-one (for example OCTALACTONE GAMMA); 1-(2-naphtalenyl)-ethanone (for example ORANGER CRYSTALS); 3-methoxy-5-methylphenol (for example ORCINYL 3); 4-(tert-pentyl)cyclohexanone (for example ORIVONE); 2-methyl-4-propyl-1,3-oxathiane (for example OXANE); (2,4a,5,8a-tetramethyl-1,2,3,4,7,8-hexahydronaphthalen-1-yl) formate (for example OXYOCTALINE FORMATE); (2-methoxyethyl)benzene (for example PANDANOL); 2-ethyl-N-methyl-N-(m-tolyl)butanamide (for example PARADISAMIDE); 5-methyl-2(2-methylethyl)-cyclohexanone (for example PARAMENTHONE); 1,1-dimethoxynon-2-yne (for example PARMAVERT); 5-heptyldihydrofuran-2(3H)-one (for example PEACH PURE); 2-methyl-4-methylene-6-phenyltetrahydro-2H-pyran (for example PELARGENE); 3,7-dimethylocta-1,6-dien-3-yl dimethylcarbamate (for example PEPPERWOOD); 2-propan-2-yloxyethylbenzene (for example PETIOLE); 2-cyclohexylhepta-1,6-dien-3-one (for example PHARAONE); 2-phenoxyacetaldehyde (for example PHENOXY ACETALDEHYDE); 2-phenyl-ethanal (for example PHENYL ACETALDEHYDE); 2-phenylacetic acid (for example PHENYL ACETIC ACID PURE); 2-phenylethyl acetate (for example PHENYL ETHYL ACETATE); 2-phenylethanol (for example PHENYL ETHYL ALCOHOL); 2-phenylethyl formate (for example PHENYL ETHYL FORMATE); 3-phenylpropanal (for example PHENYL PROPIONIC ALDEHYDE); 3-phenylpropan-1-ol (for example PHENYL PROPYL ALCOHOL); 2,6,6-trimethylbicyclo[3.1.1]hept-2-ene (for example PINENE ALPHA); 6,6-dimethyl-2-methylenebicyclo[3.1.1]heptane (for example PINENE BETA); 3-(6,6-dimethylbicyclo[3.1.1]hept-2-en-2-yl)propanal (for example PINOACETALDEHYDE); (E)-3,3-dimethyl-5-(2,2,3-trimethyl-3-cyclopenten-1-yl)-4-penten-2-ol (for example POLYSANTOL); (2E,5E)-5,6,7-trimethylocta-2,5-dien-4-one (for example POMAROSE); 3-methylbut-2-en-1-yl acetate (for example PRENYL ACETATE); 2-ethoxy-5-prop-1-enylphenol (for example PROPENYL GUAETHOL); 2-ethoxy-4-(isopropoxymethyl)phenol (for example PROPYL DIANTILIS); 5-pentyldihydrofuran-2(3H)-one (for example PRUNOLIDE); 6-(sec-butyl)quinoline (for example PYRALONE); 2-pentylcyclopentanone (for example QUINTONE); (E)-2-ethyl-4-(2,2,3-trimethylcyclopent-3-en-1-yl)but-2-en-1-ol (for example RADJANOL); 4-(4-hydroxyphenyl)butan-2-one (for example RASPBERRY KETONE); mixture of 3,7-dimethyloct-6-en-1-ol and 3,7-dimethyloct-7-en-1-ol (for example RHODINOL); 2,4-dimethyl-4-phenyltetrahydrofuran (for example RHUBAFURAN); (4aR,8aS,E)-6-ethylideneoctahydro-2H-5,8-methanochromene (for example RHUBOFLOR); 1,1-diethoxycyclohexane (for example RHUM ACETAL); 2,2,2-trichloro-1-phenylethyl acetate (for example ROSACETOL); dec-9-en-1-ol (for example ROSALVA); 4-methyl-2-(2-methylprop-1-en-1-yl)tetrahydro-2H-pyran (for example ROSE OXIDE CO and ROSE OXIDE LAEVO); 3-isobutyl-1-methylcyclohexanol (for example ROSSITOL); (1-methyl-2-(5-methylhex-4-en-2-yl)cyclopropyl)methanol (for example ROSYFOLIA); 4-methyl-2-phenyl-3,6-dihydro-2H-pyran (for example ROSYRANE SUPER); 2,3,3-trimethyl-2,3-dihydro-1H-inden-1-one (for example SAFRALEINE); 2,6,6-trimethylcyclohexa-1,3-dienecarbaldehyde (for example SAFRANAL); (E)-2-methyl-4-(2,2,3-trimethyl-1-cyclopent-3-enyl)but-2-en-1-ol (for example SANTACORE); (3aR,4R,6S,7R,7aR)-6-methoxyoctahydro-1H-4,7-methanoindene-1-carbaldehyde (for example SCENTENAL); 4-vinylcyclohex-1-enecarbaldehyde (for example SHISOLIA); 3-methyl-1H-indole (for example SKATOLE); 2',2',3,7,7-pentamethylspiro[bicyclo[4.1.0]heptane-2,5'-[1,3]dioxane] (for example SPIRAMBRENE); 1-(spiro[4.5]dec-6-en-7-yl)pent-4-en-1-one (for example SPIROGALBANONE and SPIROGALBANONE PURE); (E)-5-methylheptan-3-one oxime (for example STEMONE); (E)-6-ethyl-3-methyloct-6-en-1-ol (for example SUPER MUGUET); (E)-2-((3,5-dimethylhex-3-en-2-yl)oxy)-2-methylpropyl cyclopropanecarboxylate (for example SYLKOLIDE); 2-(p-tolyl)acetaldehyde (for example SYRINGA ALDEHYDE); (Z)-1-(cyclooct-3-en-1-yl)ethanone (for example TANAISONE); 1-methyl-4-propan-2-ylcyclohexa-1,4-diene (for example TERPINENE GAMMA); 1-methyl-4-(propan-2-ylidene)cyclohex-1-ene (for example TERPINOLENE); 3,7-dimethyloctanal (for example TETRAHYDRO CITRAL); 3,7-dimethyloctan-3-ol (for example TETRAHYDRO LINALOOL); 2,6-dimethyloctan-2-ol (for example TETRAHYDRO MYRCENOL); (E)-3,7-dimethylocta-2,6-diene-1-thiol (for example THIOGERANIOL); 2-isopropyl-5-methylphenol (for example THYMOL CRYSTALS); 4-methylbenzaldehyde (for example TOLYL ALDEHYDE PARA); 1-(cyclopropylmethyl)-4-methoxybenzene (for example TOSCANOL); 2,4-dimethylcyclohex-3-enecarbaldehyde (for example TRICYCLAL); (E)-tridec-2-enenitrile (for example TRIDECENE-2-NITRILE); 3-phenylbutanal (for example TRIFERNAL); 3-(benzo[d][1,3]dioxol-5-yl)-2-methylpropanal (for example TROPIONAL); 6-hexyltetrahydro-2H-pyran-2-one (for example UNDECALACTONE DELTA); (3E,5Z)-undeca-1,3,5-triene (for example UNDECATRIENE); (E)-4-methyldec-3-en-5-ol (for example UNDECAVERTOL); 4-hydroxy-3-methoxybenzaldehyde (for example VANILLIN); 2,2,5-trimethyl-5-pentylcyclopentanone (for example VELOUTONE); 3,4-dimethoxybenzaldehyde (for example VERATRYL ALDEHYDE); (3aS,4R,6S,7R,7aR)-6-methoxy-3a,4,5,6,7,7a-hexahydro-1H-4,7-methanoindene (for example VERDALIA); 2-(tert-butyl)cyclohexanol (for example VERDOL); 1-((1S,8aS)-1,4,4,6-tetramethyl-2,3,3a,4,5,8-hexahydro-1H-5,8a-methanoazulen-7-yl)ethanone (for example VERTOFIX COEUR); 2,4-diethoxy-5-methylpyrimidine (for example VETHYMINE); (5R,10R)-6,10-dimethyl-2-(propan-2-ylidene)spiro[4.5]dec-6-en-8-ol (for example VETIVENOL); (4,8-dimethyl-2-propan-2-ylidene-3,3a,4,5,6,8a-hexahydro-1H-azulen-6-yl) acetate (for example VETIVERYL ACETATE); (2E,6Z)-nona-2,6-dienenitrile (for example VIOLET NITRILE); 2-methoxynaphthalene (for example YARA YARA); 2-(2,4-dimethylcyclohexyl)pyridine (for example ZINARINE); and essential oils (for example CEDARWOOD OIL, CLOVE BUD OIL, CURGIX, EUCALYPTUS OIL, GERANIUM OIL, GRAPEFRUIT OIL, GUAIACWOOD OIL, LAVANDIN OIL, LAVENDER OIL, LIME OXIDE, LIME TERPENES, LITSEA CUBEBA OIL, METHYLIONANTHEME, NUTMEG OIL INDONESIA, ORANGE OIL, ORANGE TERPENES, PATCHOULI OIL, PETITGRAIN OIL, SPEARMINT OIL, TURPENTINE OIL, YLANG).

Whether the high odour intensity ingredients can be considered to be neutral or non-perfumistic in context can then be tested in an objective and straightforward manner, following the test protocol set forth below:
1. 20 µL of a test fragrance at the same concentration that was shown to have an odour intensity score of 100 or more in accordance with the odour intensity test protocol referred to above, is applied to a clean sanitary or incontinence article and the article placed in a 500 ml wide-top, lidded glass jar.
2. The sanitary or incontinence article is olfactively assessed by a panel of at least 20 volunteers. Each volunteer selects the most appropriate statement from the following:
   a. Fragrance is present and I am sure
   b. Fragrance is present but I am less sure
   c. Fragrance is not present but I am less sure
   d. Fragrance is not present and I am sure A test fragrance is considered to be neutral or 'non-perfumistic' in the context of being smelled with an article, if less than 50% of the panellists are sure that a fragrance is present (i.e. less than 50% of panellists selected response 'a').

The skilled person will appreciate from the foregoing that a list of suitable, neutral or non-perfumistic fragrance ingredients or fragrance compositions useful in the operation of the present invention can be easily determined in a straightforward manner. A list of non-perfumistic fragrance ingredients may be selected from the group consisting of 4-(tert-pentyl)cyclohexanone (for example ORIVONE); 4-(tert-butyl)cyclohexyl acetate (Para-tert-butyl-cyclohexyl acetate; PTBCHA); 2,3,3-trimethyl-2,3-dihydro-1H-inden-1-one (for example SAFRALEINE); (3aR,6S,7aS)-3a,4,5,6,7,7a-hexahydro-1H-4,7-methanoinden-6-yl acetate (for example JASMACYCLENE); (Z)-3,4,5,6,6-pentamethylhept-3-en-2-one (for example KOAVONE); (E)-4-(2,6,6-trimethylcyclohex-2-en-1-yl)but-3-en-2-one (for example IRISONE PURE); ethyl 6-acetoxyhexanoate (for example BERRYFLOR); benzyl acetate; hexyl 2-hydroxybenzoate (for example Hexyl Salicylate); (E)-4-(2,6,6-trimethylcyclohex-1-en-1-yl)but-3-en-2-one (for example IONONE BETA); 8-methyl-1-oxaspiro[4.5]decan-2-one (for example METHYL LAITONE); 1-(3-methylbenzofuran-2-yl)ethanone (for example NEROLIONE); 7-isopropyl-8,8-dimethyl-6,10-dioxaspiro[4.5]decane (for example OPALAL); 2-cyclohexylidene-2-phenylacetonitrile (for example PEONILE); 3-((1R,2S,4R,6R)-5,5,6-trimethylbicyclo[2.2.1]heptan-2-yl)cyclohexanol (for example SANDELA); 1,4-dioxacycloheptadecane-5,17-dione (for example ETHYLENE BRASSYLATE); and 8-ethyl-1-oxaspiro[4.5]decan-2-one (for example ETHYL LAITONE), and glycol ethers, for example any of those known and commercially available under the DOWANOL brand.

Examples of particularly useful fragrance ingredients that are considered neutral or non-perfumistic when smelled in the context of an article to which it is intended to be applied include:

2,3,3-trimethyl indanone, commercially available from Givaudan under the trade name SAFRALEINE™; 4-(2-methylbutan-2-yl)cyclohexan-1-one, commercially available from IFF under the trade name of ORIVONE™; and (4-tert-butylcyclohexyl) acetate (CAS No. 32210-23-4 104-05-2), commercially available from a number of suppliers and commonly referred to by the abbreviation PTBCHA. 2,3,3-trimethyl indanone (SAFRALEINE™) is particularly suitable.

It is a feature of the present invention that because the odour of the neutral or non-perfumistic ingredients, in the context of incontinence or sanitary articles, is not perceived as belonging to a fragrance as such by panellists, they can be used in the fragrance compositions at relatively high concentrations. The use of non-perfumistic ingredients is particularly advantageous for use in adult incontinence articles, as they allow for preventing any noticeable odours—be it malodour or fragrance.

In the normal course of fragrance creation for the fragrance compositions intended for use in incontinence or sanitary articles, the skilled person would avoid using very high levels of ingredients having relatively high odour intensity, given the prejudice in the art. However, having regard to the teaching of the present invention, the applicant has discovered a means of loading fragrance compositions with relative high odour intensity fragrance ingredients to exert an efficacious malodour-counteracting effect, without creating an odour impression that would be perceived by consumers as being overtly "perfumistic".

A fragrance composition according to the present invention contains one or more of the non-perfumistic fragrance ingredients, such as any of those referred to specifically herein.

In an embodiment of the present invention, the fragrance composition comprises up to 100 weight percent (wt %) based on the total weight of the fragrance composition of at least one non-perfumistic fragrance ingredient, such as those referred to herein above, more particularly 20 to 100 wt %, 30 to 100 wt %, 40 to 100 wt %, 50 to 100 wt %, 60 to 100 wt %, 70 to 100 wt %, 80 to 100 wt %, and more particularly still 90 to 100 wt %.

Given the fact that fragrance compositions of the present invention can contain relatively high levels of the neutral or non-perfumistic fragrance ingredients, the perfumer may find the latitude to incorporate relatively low levels of known efficacious deodorizing fragrance ingredients that themselves would be considered to be perfumistic, but which, when incorporated into the fragrance compositions at low levels, can nevertheless form part of the fragrance composition.

As used herein, the term 'perfumistic' is used to describe a fragrance ingredient that, when employed at levels that provide a deodorizing effect in a fragrance composition, would clearly be perceived by a consumer as having an odour that is clearly fragrant and not part of the odour of the article as such, or its packaging.

A fragrance composition containing at least one 'non-perfumistic' fragrance ingredient as well as at least one perfumistic fragrance ingredient that is used at relatively low levels forms a particular embodiment of the invention.

Perfumistic fragrance ingredients may be employed in fragrance compositions of the present invention, but they should be used at relatively low levels. More particularly, they may be employed at levels from 0 to 50 wt %, and more particularly 0 to 20 wt %, more particularly still 0 to 10 wt %.

Additional 'perfumistic' fragrance ingredients may be any of those commonly used by perfumers. Such fragrance ingredients include any of those mentioned in standard perfumery reference works, such as S. Arctander, Perfume and Flavor Chemicals (Montclair, N.J., 1969); S. Arctander, Perfume and Flavor Materials of Natural Origin (Elizabeth N.J. 1960); and in "Flavor and Fragrance Materials—1991", Allured Publishing Company Wheaton Ill. USA, or in any later editions of those titles, which are herein incorporated by reference.

Additional fragrance ingredients may be chosen primarily for their hedonic properties, or they may be selected primarily for their malodour-counteracting properties, whether they are inhibitory or masking of malodours.

Examples of such perfume ingredients include, but are not limited to, N-ethyl-N-(3-methylphenyl) propionamide (for example AGARBOIS), decanal (for example ALDEHYDE C 10); undecanal (for example ALDEHYDE C 110 UNDECYLIC and ALDEHYDE C 11); dodecanal (for example ALDEHYDE C 12); 2-methylundecanal (for example ALDEHYDE C 12 MNA); hexanal (for example ALDEHYDE C 6); heptanal (for example ALDEHYDE C 7); octanal (for example ALDEHYDE C 8); 3,5,5-trimethylhexanal (for example ALDEHYDE C 9 ISONONYLIC); nonanal (for example ALDEHYDE C 9 NONYLIC); allyl 3-cyclohexylpropionate (for example ALLYL CYCLOHEXYL PROPIONATE); allyl hexanoate; allyl heptanoate (for example ALLYL OENANTHATE); pentyl butanoate (for example AMYL BUTYRATE); pentyl 2-hydroxybenzoate (for example AMYL SALICYLATE); 4-methoxybenzaldehyde (for example ANISIC ALDEHYDE); benzaldehyde; 8-(sec-butyl)-5,6,7,8-tetrahydroquinoline (for example BIGARYL); (1S,4S)-1,7,7-trimethylbicyclo[2.2.1]heptan-2-one (for example CAMPHOR); (5R)-2-methyl-5-prop-1-en-2-ylcyclohex-2-en-1-one (for example CARVONE LAEVO); methyl 2-(3-oxo-2-pentylcyclopentyl)acetate (for example CEPIONATE); (2E)-3-phenylprop-2-enal (for example CINNAMIC ALDEHYDE); (Z)-hex-3-en-1-ol (CIS-3-HEXENOL); (Z)-hex-3-enyl acetate (CIS-3-HEXENYL ACETATE); (E)-3,7-dimethylocta-2,6-dienal (for example CITRAL); 3,7-dimethyloct-6-enal (for example CITRONELLAL); 3,7-dimethyloct-6-en-1-ol (for example CITRONELLOL); 2,4-dimethylcyclohex-3-ene-1-carbaldehyde (for example CYCLAL C); 1-methyl-4-propan-2-ylbenzene (for example CYMENE PARA); 1-(2,6,6-trimethyl-1-cyclohex-3-enyl)but-2-en-1-one (for example DAMASCONE DELTA); 1-allyl-4-methoxybenzene (for example ESTRAGOLE); ethyl 2-methylbutanoate (ETHYL 2-METHYL BUTYRATE); ethyl acetate; ethyl butanoate (ETHYL BUTYRATE); ethyl hexanoate; ethyl 3-methylbutanoate (ETHYL ISOVALERATE); ethyl heptanoate (for example ETHYL OENANTHATE); (1s,4s)-1,3,3-trimethyl-2-oxabicyclo[2.2.2]octane (for example EUCALYPTOL); 1-phenylethyl acetate (for example GARDENOL); (E)-3,7-dimethylocta-2,6-dien-1-ol (for example GERANIOL); (E)-3,7-dimethylocta-2,6-dienenitrile (for example GERANYL NITRILE); hexyl acetate; hexyl 2-methylpropanoate (HEXYL ISOBUTYRATE); (E)-4-(2,6,6-trimethylcyclohex-1-en-1-yl)but-3-en-2-one (for example IONONE BETA); 3-methylbutyl acetate (ISOAMYL ACETATE); 2-methylpropyl 2-methylpropanoate (ISOBUTYL ISOBUTYRATE); 6-butan-2-yl-quinoline (ISOBUTYL QUINOLINE); isopropyl 2-methylbutanoate (ISOPROPYL 2-METHYL BUTYRATE); (2E,6Z)-3,7-dimethylnona-2,6-dienenitrile (for example LEMONILE); 3,7-dimethylocta-1,6-dien-3-ol (for example LINALOOL); 2-isopropyl-5-methylcyclohexanol (for example MENTHOL); heptan-2-one (METHYL AMYL KETONE); methyl benzoate; 6-methylhept-5-en-2-one (METHYL HEPTENONE); octan-2-one (METHYL HEXYL KETONE); 2-methyl-decanal (METHYL OCTYL ACETALDEHYDE); methyl 2-hydroxybenzoate (METHYL SALICYLATE); 2-phenylethyl acetate (PHENYL ETHYL ACETATE); (2E,5E)-5,6,7-trimethylocta-2,5-dien-4-one (for example POMAROSE); 3-methylbut-2-en-1-yl acetate (for example PRENYL ACETATE); 4-methyl-2-(2-methylprop-1-en-1-yl)tetrahydro-2H-pyran (for example ROSE OXIDE); 4-methyl-2-phenyl-3,6-dihydro-2H-pyran (for example ROSYRANE SUPER); 1-methyl-4-(propan-2-ylidene)cyclohex-1-ene (for example TERPINOLENE); 2,6-dimethyloctan-2-ol (for example TETRAHYDRO MYRCENOL); (E)-hex-2-enal (TRANS-2-HEXENAL); (E)-dec-4-enal (TRANS-4-DECENAL); 2,4-dimethylcyclohex-3-enecarbaldehyde (for example TRICYCLAL); and (3E,5Z)-undeca-1,3,5-triene (UNDECATRIENE); and essential oils (for example ORANGE OIL, ORANGE TERPENES DISTILLED, GERANIUM OIL, LAVANDIN, SPIKE LAVENDER, BASIL, BERGAMOT, GRAPEFRUIT OIL, LAVANDER, LIME OIL, MANDARIN OIL, PEPPERMINT OIL, PATCHOULI OIL, PETITGRAIN OIL, PINE OIL, ROSEMARY OIL, SPEARMINT OIL, TANGERINE OIL, YLANG OIL, CINNAMON, CLOVE OIL).

In a particular embodiment, the fragrance composition of the present invention comprises one or more ingredients selected from the group consisting of Jasmacyclene, Orivone, PTBCHA, Safraleine, Irisone Pure, and Agarbois, preferably at least two of these ingredients, and more preferably at least three of these ingredients.

The fragrance compositions of the present invention may be applied to an article in the form of neat oil, as such. However, since fragrance oils are relatively expensive and because, when uncontained, they can dissipate quickly overtime, it may be desirable to encapsulate them in a suitable vehicle.

Accordingly, the invention provides in a particular embodiment a fragrance composition substantially as hereinabove described in neat oil form, in encapsulated form, or a mixture of both neat oil and encapsulated form.

In principle, any fragrance encapsulating technology may be employed in the present invention. However, considering that it is generally desirable that odour intensity is kept to a minimum, it is preferred to encapsulate the fragrance composition in an encapsulating medium that is activated to release upon sensing moisture. In this way, the article has low odour, or no discernible odour, in the dry state, and only emanates the fragrance composition when subjected to moisture. Essentially, any encapsulation technology that has been proposed for use in incontinence or sanitary products, and other disposable absorbent articles, such as disclosed in U.S. Pat. Nos. 5,733,272 or 5,429,628, may be employed in pursuance of the present invention.

Furthermore, the perceived intensity of the fragrance composition may be further modulated by incorporating it into a delivery vehicle, which is adapted to release fragrance in a controlled manner over time, or in response to an external stimulus, such as contact with moisture. Suitable delivery vehicles include known starch encapsulation technology.

In a particular embodiment of the present invention, the fragrance composition is encapsulated in a modified starch capsule.

Starches suitable for encapsulating the fragrance compositions of the present invention can be made from raw starch, pre-gelatinized starch, modified starch derived from tubers, legumes, cereal and grains, for example corn starch, wheat starch, rice starch, waxy corn starch, oat starch, cassava starch, waxy barley, waxy rice starch, sweet rice starch, amioca, potato starch, tapioca starch, oat starch, and mixtures thereof.

Modified starches suitable for use as the encapsulating matrix in the present invention include hydrolyzed starch, acid thinned starch, starch esters of long chain hydrocarbons, starch acetates, starch octenyl succinate, and mixtures thereof.

The term "hydrolyzed starch" refers to oligosaccharide-type materials that are typically obtained by acid and/or enzymatic hydrolysis of starches, preferably corn starch. Suitable hydrolyzed starches for inclusion in the present invention include maltodextrins and corn syrup solids. The hydrolyzed starches for inclusion with the mixture of starch esters have a Dextrose Equivalent (DE) value of from about 10 to about 36 DE. The DE value is a measure of the reducing equivalence of the hydrolyzed starch referenced to dextrose and expressed as a percent (on a dry basis). The higher the DE value, the more reducing sugars present. A method for determining DE values can be found in Standard Analytical Methods of the Member Companies of Corn Industries Research Foundation, 6th ed. Corn Refineries Association, Inc. Washington, D.C. 1980, D-52.

Starch esters having a degree of substitution in the range of from about 0.01% to about 10.0% may be used to encapsulate the malodour-controlling composition of the present invention. The hydrocarbon part of the modifying ester should be from a C5 to C16 carbon chain. Preferably, octenylsuccinate (OSAN) substituted waxy corn starches of various types such as 1) waxy starch: acid thinned and OSAN substituted, 2) blend of corn syrup solids: waxy starch, OSAN substituted, and dextrinized, 3) waxy starch: OSAN substituted and dextrinized, 4) blend of corn syrup solids or maltodextrins with waxy starch: acid thinned OSAN substituted, and then cooked and spray dried, 5) waxy starch: acid thinned and OSAN substituted then cooked and spray dried, and 6) the high and low viscosities of the above modifications (based on the level of acid treatment) can also be used in the present invention.

Modified starches having emulsifying and emulsion stabilizing capacity such as starch octenyl succinates have the ability to entrap the composition droplets in the emulsion due to the hydrophobic character of the starch modifying agent. The composition remains substantially trapped in the modified starch until exposed to moisture.

The fragrance compositions of the present invention may be applied to all manner of sanitary and incontinence articles that are utilized to absorb body fluids and human waste. Typically, such articles are absorbent articles adapted to be placed on, in or about the human body, and include infant diapers, feminine care products, and adult incontinence products. Such products may be provided, for example, as briefs, undergarments, pads, guards, slip-ons, inserts and the like.

Fragrance compositions of the present invention are particularly effective at reducing or eliminating malodour caused by or associated with body fluids, and particularly urine when incorporated into articles at levels from 0.2 mg per article up to 100 mg per article.

There now follows a series of examples that serve to illustrate the invention.

EXAMPLE 1: ODOUR INTENSITY TEST 1.5 g each of a number of fragrance ingredients and fragrance compositions (described below) having a recognisable olfactive character was assessed for intensity versus 5% benzyl acetate normalised to an intensity score of 100:
PTBCHA (100%);
a coconut fragrance composition (2.5% dilution);
jasmacyclene (10% dilution);
Safraleine™ (10% dilution);
an apricot fragrance composition (10% dilution);
a plum fragrance composition (5% dilution);
orivone (100%);
a peach fragrance composition (20% dilution);
a berry fragrance composition;
a lavender fragrance composition (50% dilution); and
benzyl acetate (5% dilution).

Normalized odour intensity data for the fragrance compositions and fragrance ingredients are shown in FIG. 1. The results show that coconut and berry each have too low an odour intensity to be considered for non-perfumistic/perfumistic character evaluation.

EXAMPLE 2: ESTABLISHING THE 'NON-PERFUMISTIC' CHARACTER OF A FRAGRANCE

Figure 2:
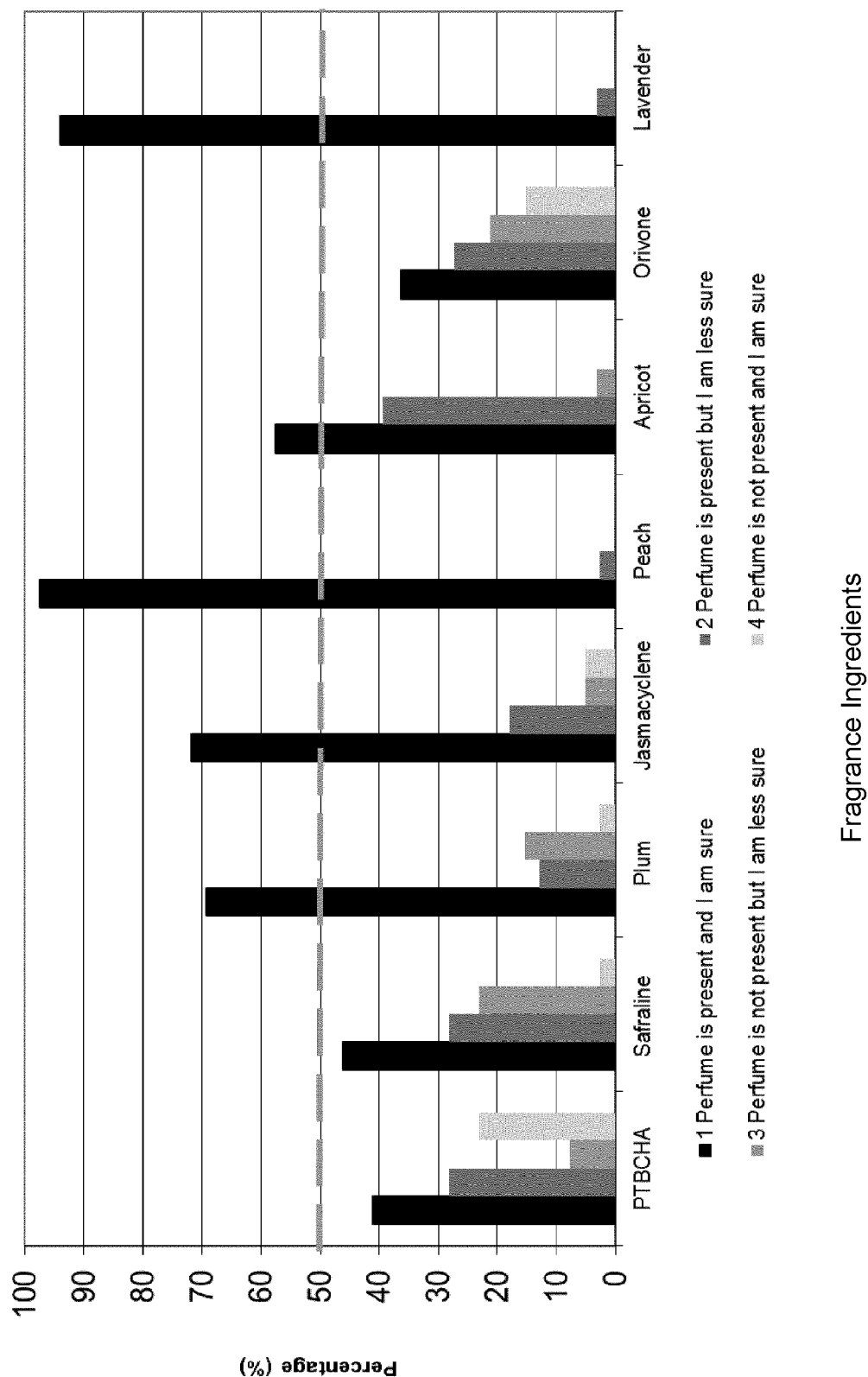
FIG. 2 depicts olfactory assessment data relevant reported by 28 volunteers.

20 μL of test fragrance ingredients and fragrance compositions, previously shown in accordance with Example 1 to have intensity scores of 100 or more, were applied to individual clean sanitary or incontinence articles and the articles placed into individual 500 ml wide-top lidded glass jars. The sanitary or incontinence articles were olfactively assessed by a panel of 28 volunteers. The volunteers were each asked to select the most appropriate statement from the following:

a. Perfume is present and I am sure
b. Perfume is present but I am less sure
c. Perfume is not present but I am less sure
d. Perfume is not present and I am sure The results, shown in FIG. 2, demonstrate that less than 50% of volunteers were sure that a perfume was present when Safraleine™, orivone and PTBCHA were applied to the incontinence article. These fragrance ingredients are, therefore, considered to be 'non-perfumistic' within the meaning of the present invention.

EXAMPLE 3: MALODOUR CONTROL

20 μL PTBCHA (neat, 20%, and 50% dilutions) were applied to separate incontinence articles. 50 mL of microbially contaminated human urine was then applied to each incontinence article and the articles placed into individual 500 ml wide-top lidded glass jars and incubated for 4 hours. The jars were then assessed for malodour by a trained sensory panel.

Figure 3:
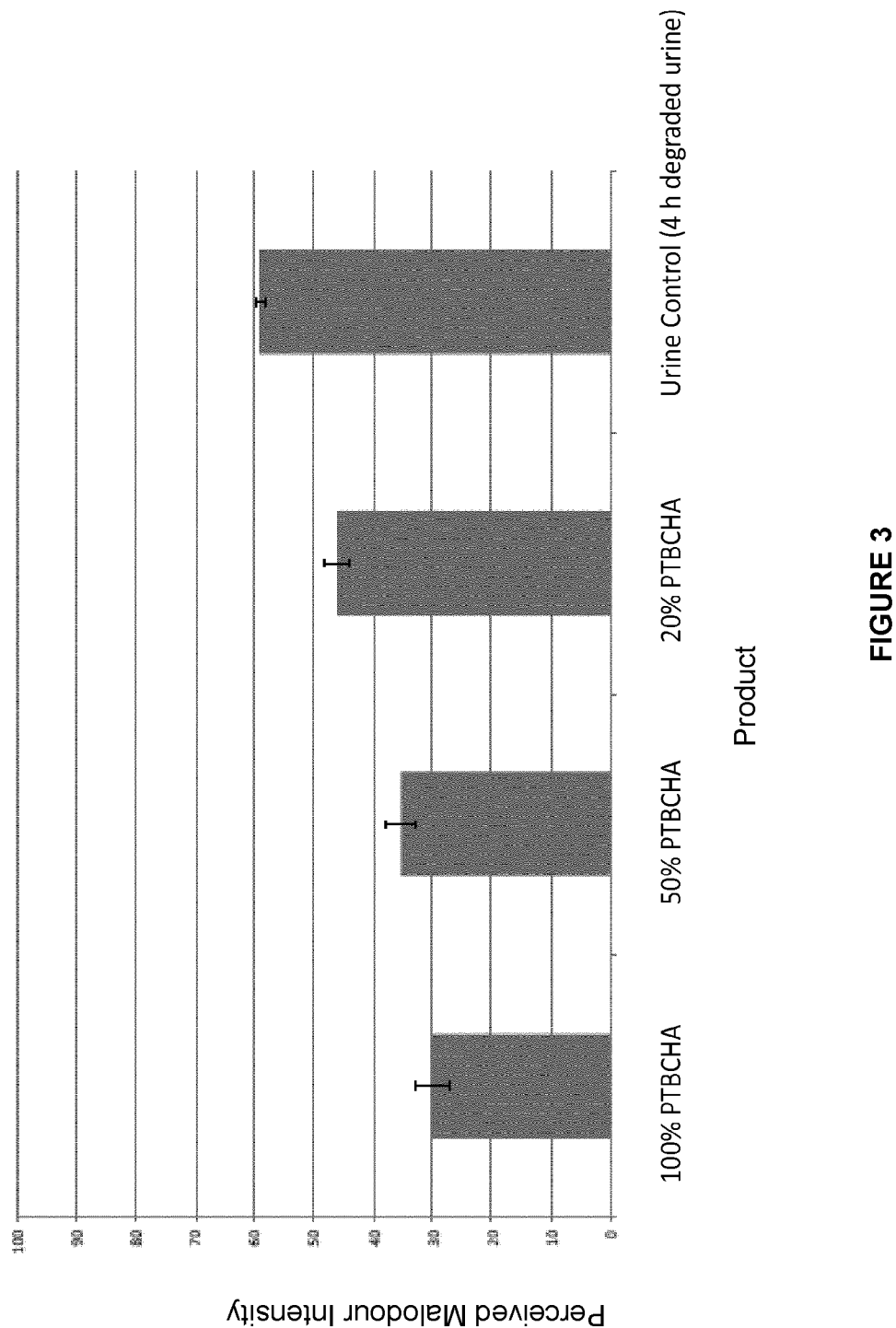
FIG. 3 depicts data of Table 1 relevant to perceived malodour intensity at varied concentrations of PTBCHA.

The results are shown in Table 1 and FIG. 3, which demonstrate that increasing concentrations of PTBCHA reduce perceived malodour intensity. 100% PTBCHA shows the greatest reduction in malodour even though, at this level, less than 50% of volunteers are sure a fragrance is present.

TABLE 1

| Products | Perceived Malodour Intensity (mean ± standard error of the mean) | Significance of Differences* |
|---|---|---|
| 100% PTBCHA | 30.0 ± 3.1 | A |
| 50% PTBCHA | 35.3 ± 2.5 | A |
| 20% PTBCHA | 46.2 ± 2.1 | B |
| Urine Control (4 h degraded urine) | 59.1 ± 0.7 | C |

(*The same letter means that there are no statistically significant differences between the relevant figures.)

EXAMPLE 4: MALODOUR CONTROL

20 μL Orivone™ (neat, 20% and 50% dilutions) were applied to separate incontinence articles. 50 mL of microbially contaminated human urine was then applied to each incontinence article and the articles placed into individual 500 ml wide-top lidded glass jars and incubated for 4 hours. The jars were then assessed for malodour by a trained sensory panel.

Figure 4:
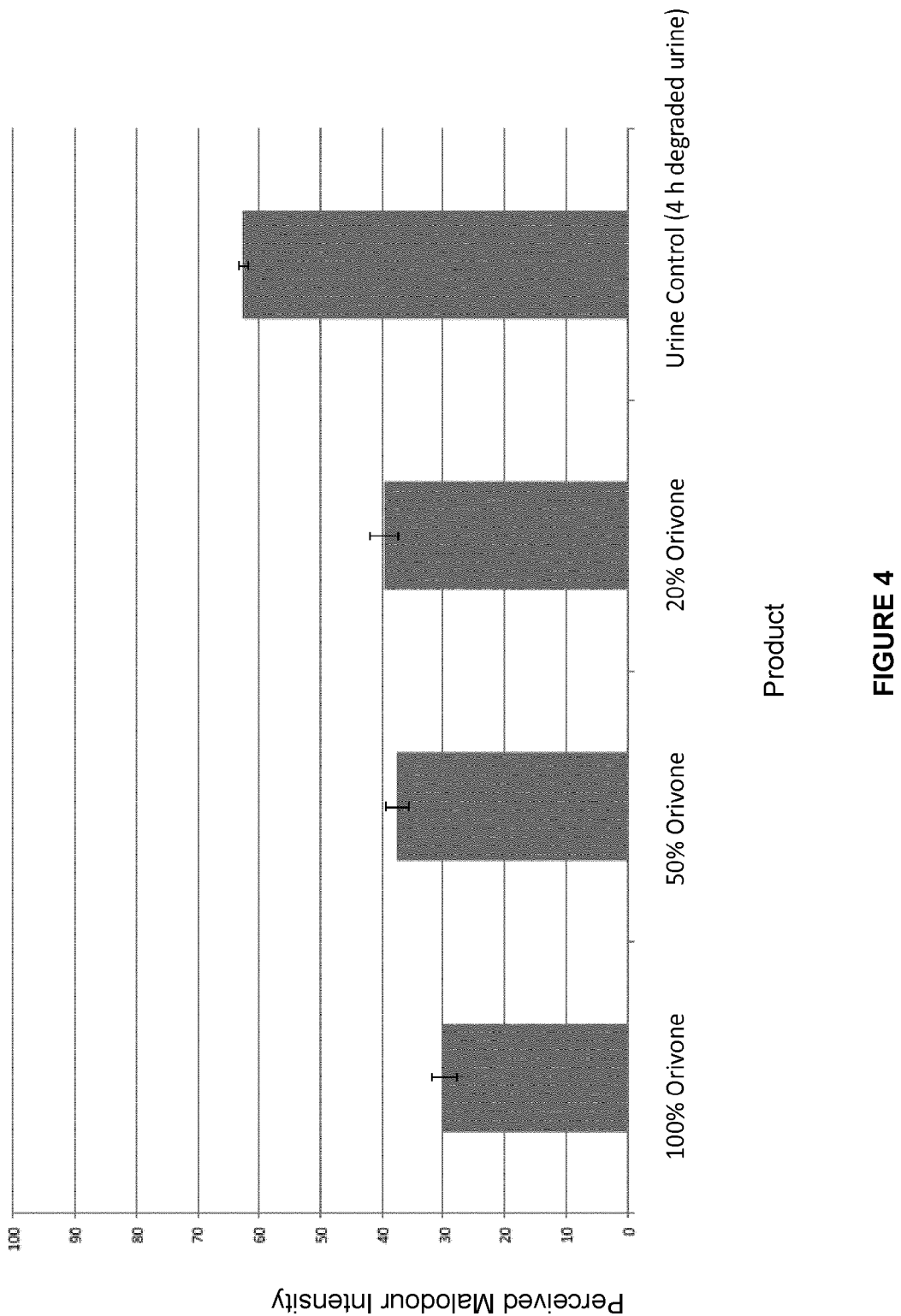
FIG. 4 depicts data of Table 2 relevant to perceived malodour intensity at varied concentrations of ORIVONE.

The results are shown in Table 2 and FIG. 4, which demonstrate that increasing concentrations of Orivone™ reduce the perceived malodour intensity. 100% Orivone™ shows the greatest reduction in malodour even though, at this level, less than 50% of volunteers are sure a fragrance is present.

TABLE 2

| Products | Perceived Malodour Intensity (mean ± standard error of the mean) | Significance of Differences* |
|---|---|---|
| 100% Orivone ™ | 30.0 ± 2.0 | A |
| 50% Orivone ™ | 37.5 ± 2.0 | B |
| 20% Orivone ™ | 39.6 ± 2.2 | B |
| Urine Control (4 h degraded urine) | 62.6 ± 0.8 | C |

(*The same letter means that there are no statistically significant differences between the relevant figures.)

EXAMPLE 5: MALODOUR CONTROL

20 μL Safraleine™ (neat and DPG dilutions) were applied to separate incontinence articles. 50 mL microbially contaminated human urine was then applied to each incontinence article and the articles placed into individual 500 ml wide-top lidded glass jars and incubated for 4 hours. The jars were then assessed for malodour by a trained sensory panel.

Figure 5:
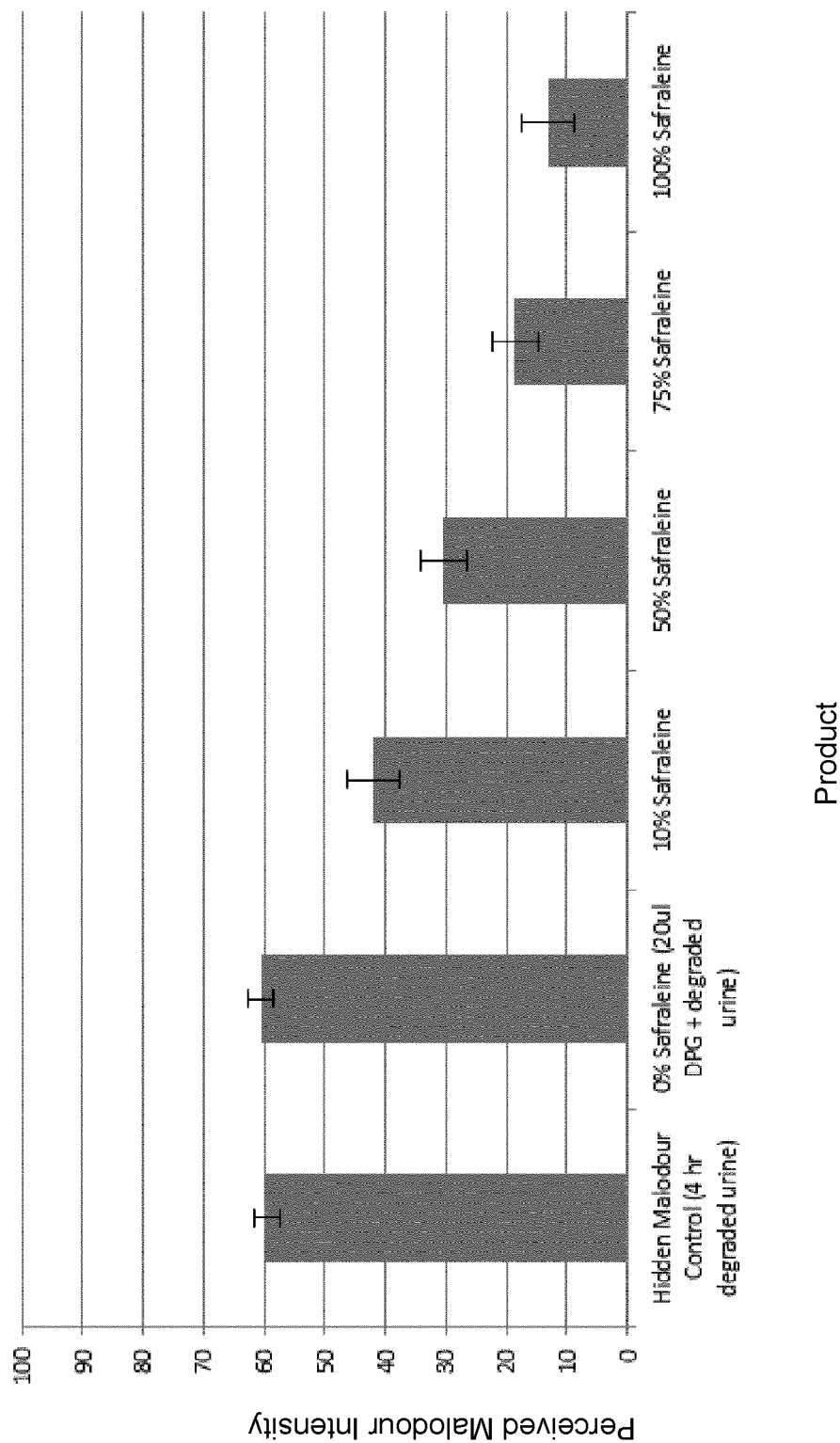
FIG. 5 depicts data of Table 3 relevant to perceived malodour intensity at varied concentrations of SAFRALEINE.

The results are shown in Table 3 and FIG. 5, which demonstrate that increasing concentrations of Safraleine™ reduce perceived malodour intensity. 100% Safraleine™ shows the greatest reduction in malodour even though at this level less than 50% of volunteers are sure that a fragrance is present.

TABLE 3

| Products | Perceived Malodour Intensity (mean ± standard error of the mean) | Significance of Differences* |
|---|---|---|
| Hidden Malodour Control (4 h degraded urine) | 59.5 ± 2.1 | A |
| 0% Safraleine ™ (20 μl DPG + degraded urine) | 60.5 ± 2.1 | A |
| 10% Safraleine ™ | 41.8 ± 4.3 | B |
| 50% Safraleine ™ | 30.5 ± 3.8 | B |
| 75% Safraleine ™ | 18.6 ± 3.8 | C |
| 100% Safraleine ™ | 13.2 ± 4.4 | C |

(*The same letter means that there are no statistically significant differences between the relevant figures.)

The invention claimed is:

1. A sanitary or incontinence article fragrance composition used in the treatment of malodour caused by or associated with human body fluids, wherein said fragrance composition has an odour that is reminiscent of the odour of the article, or that is reminiscent of the odour of a packaging material for said article, wherein the fragrance composition comprises 2,3,3-trimethyl indanone (SAFRALEINE) as a fragrance ingredient.

2. A sanitary or incontinence article fragrance composition according to claim 1, further comprising at least one fragrance ingredient selected from the group consisting of: 4-(2-methylbutan-2-yl)cyclohexan-1-one; para-tertiary butyl cyclohexyl acetate; and mixtures thereof.

3. A sanitary or incontinence article according to claim 2.

4. A sanitary or incontinence article fragrance composition according to claim 1, wherein said at least one fragrance ingredient is present in an amount of about 20 to 100 wt % of the fragrance composition.

5. A sanitary or incontinence article comprising a fragrance composition according to claim 1.

6. The sanitary or incontinence article according to claim 5, which is a urinary incontinence treatment article.

7. A method of preventing or ameliorating malodour caused by or associated with human body fluids, said method comprising the step of providing a sanitary or incontinence article according to claim 5 with instructions to place the article on, in or about the human body proximate to a body waste discharge area.

8. A method of promoting cleanliness, hygiene and/or well-being in an incontinent population, said method comprising the step of providing an incontinence article according to claim 5 with instructions to place the article on, in or about the human body proximate to a body waste discharge area.

9. The method of claim 8, wherein the incontinent population is a female population.

10. A method of preparing a fragrance composition adapted for use with a sanitary or incontinence article in the treatment of malodour caused by or associated with human body fluids, wherein said method comprises the step of: selecting at least one fragrance ingredient according to claim 1.

11. A sanitary or incontinence article comprising a fragrance composition according to claim 1.

12. A sanitary or incontinence article according to claim 11, wherein said at least one fragrance ingredient is present in an amount of about 20 to 100 wt % of the fragrance composition.

13. A method of preventing or ameliorating malodour caused by or associated with human body fluids, said method comprising the step of providing a sanitary or incontinence article according to claim 11 with instructions to place the article on, in or about the human body proximate to a body waste discharge area.

* * * * *